United States Patent [19]

Kröner

[11] 4,218,393

[45] Aug. 19, 1980

[54] MANUFACTURE OF VINYL-LACTONITRILE

[75] Inventor: Michael Kröner, Mannheim, Fed. Rep. of Germany

[73] Assignee: BASF Aktiengesellschaft, Fed. Rep. of Germany

[21] Appl. No.: 855,877

[22] Filed: Nov. 30, 1977

[30] Foreign Application Priority Data

Dec. 9, 1976 [DE] Fed. Rep. of Germany ....... 2655715

[51] Int. Cl.$^2$ ........................................... C07C 120/00
[52] U.S. Cl. ................................................. 260/465.6
[58] Field of Search ..................................... 260/465.6

[56] References Cited

U.S. PATENT DOCUMENTS

| | | | |
|---|---|---|---|
| 2,166,600 | 7/1939 | Leupold et al. | 260/465.6 |
| 2,188,340 | 1/1940 | Dykstra | 260/465.6 X |
| 2,537,814 | 1/1951 | Davis | 260/465.6 |

FOREIGN PATENT DOCUMENTS

| | | | |
|---|---|---|---|
| 691621 | 4/1940 | Fed. Rep. of Germany . | |
| 694942 | 7/1940 | Fed. Rep. of Germany | 260/465.6 |
| 482300 | 3/1938 | United Kingdom | 260/465.6 |
| 958896 | 5/1964 | United Kingdom | 260/465.6 |

OTHER PUBLICATIONS

Stewart, et al.; J.A.C.S., 62(1940), pp. 3281–3285.
Jones, J. Chem. Soc., 105(1914), pp. 1560–1564.
Houben–Weyl, Methoden der Organischen Chemie, vol. 8, pp. 274–277 (1952).
Kogyo Kagaku Zasshi, (60), 1957, No. 4, pp. 433–435.

*Primary Examiner*—Joseph Paul Brust
*Attorney, Agent, or Firm*—Keil & Witherspoon

[57] ABSTRACT

A new process for the manufacture of vinyl-lactonitrile by reacting methyl vinyl ketone with liquid hydrogen cyanide in the presence of basic compounds and of certain amounts of solvents. The products are starting materials for the manufacture of drugs, crop protection agents, dyes, plastics and synthetic resins.

10 Claims, No Drawings

MANUFACTURE OF VINYL-LACTONITRILE

The present invention relates to a new process for the manufacture of vinyl-lactonitrile by reacting methyl vinyk ketone with liquid hydrogen cyanide in the presence of basic compounds and of certain amounts of solvents.

Houben-Weyl, Methoden der Organischen Chemie, volume 8, pages 274–277, discloses that aldehydes and ketones can be reacted with liquid hydrogen cyanide in the presence of alkaline reagents, to give cyanohydrins. Examples of catalysts mentioned are potassium cyanide, potassium carbonate, calcium cyanide, ammonia and organic bases. It is stated that in this reaction unsaturated ketones give $\beta$-cyanoketones. The above process is described as the simplest method (method 1), which gives a good yield, when compared with reaction with nascent hydrogen cyanide (method 2), with alkali metal bisulfite and alkali metal cyanide solution (method 3) or with another cyanohydrin (method 4), but it is stated, in general terms, that it requires anhydrous or highly concentrated hydrogen cyanide. The formation of the cyanohydrin is highly exothermic and only proceeds to an equilibrium (page 275) which depends on the carbonyl compound employed, the solvent and the temperature. In the case of acetone-cyanohydrin, acetone is described as the solvent. A similar method is disclosed in U.S. Pat. No. 2,537,814 where water is added in the form of an aqueous potassium carbonate solution.

German Pat. No. 691,621 discloses reacting vinyl methyl ketone in the presence of organic, inert solvents. Toluene, pentane, cyclohexane, ether and chlorinated hydrocarbons are merely mentioned as solvents, whilst benzene, in an amount of 1.93 moles per mole of vinyl methyl ketone, is used in the Examples. The said patent shows that the critical reaction parameter is the temperature. The solvents are expressly stated to be used as diluents. If the reaction is carried out at from 15° to 80° C., with or without addition of solvents, levulonitrile is obtained, in high yield, as the end product. It is apparent from the said patent that only the reaction temperature is important in the production of the cyanohydrin and the solvent does not contribute to increasing the yield of cyanohydrin, since the patent draws attention to the identical results obtained in producing levulonitrile with and without addition of solvents.

An article in Kogyo Kagaku Zasshi, 60 (1957), No. 4, 433–435, describes a reaction with 0.84 mole of methanol and 0.09 mole of water and 1 mole of hydrogen cyanide per mole of methyl vinyl ketone at −5° C., with sodium carbonate as the catalyst. The yield is 81.7 percent if $K_2CO_3$ is employed as the catalyst, and at −9° to −12° C. the yield is 83.5% of theory. Methanol is used as the diluent, to avoid local overheating and resulting changes in the reaction product.

An article in J. Chem. Soc., 105 (1914), 1,564 discloses that in the reaction of acetone with hydrogen cyanide, the addition of water and, to a lesser extent, the addition of alcohol, lowers the yield. It is pointed out that the solvent added not only serves as a diluent but in addition shifts the reaction equilibrium in the direction of the starting materials, and thus exerts a specific dissociative effect on the cyanohydrin formed. A publication in J. Am. Chem. Soc. 62 (1940), 3,281–3,285 also discloses that acetone-cyanohydrin dissociates substantially in very dilute solutions of water, dioxane, methanol, ethanol, butanol, 2-methylpropanol and 1,1-dimethylethanol, as well as in carbon tetrachloride or benzene in the presence of amines. In many cases the amine additionally catalyzes the dissociation. German Pat. No. 694,942 expressly states that in the reaction of acetone with hydrogen cyanide in the presence of calcium cyanide as the catalyst, only very small amounts of water are allowed to be present; in the Example, 5 parts of water are stated to be present per 270 parts of hydrogen cyanide and 580 parts of acetone.

I have found that vinyl-lactonitrile of the formula

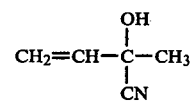

is obtained in an advantageous manner by reacting methyl vinyl ketone with hydrogen cyanide in the presence of a basic compound as catalyst and in the presence of solvents if the reaction is carried out with liquid hydrogen cyanide, in an amount of from 1 to 1.2 moles per mole of methyl vinyl ketone, in the pressure of from 50 to 1,500 percent by weight of a compound of the formula $$R^1{-}O{-}R^2 \qquad\qquad II$$

where $R^1$ is an aliphatic radical of 1 to 12 carbon atoms, $R^2$ is an aliphatic radical of 1 to 6 carbon atoms or is hydrogen or is

and $R^1$ and $R^2$ may also together be $-CH_2-CH_2-CH_2-CH_2-$ or $-CH_2-CH_2-O-CH_2-CH_2-$, and/or in the presence of from 3 to 100 percent by weight of water and/or in the presence of from 10 to 1,000 percent by weight of a carboxylic acid amide of the formula

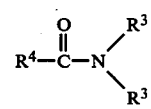

where the individual radicals $R^3$ and $R^4$ may be identical or different and each is hydrogen or an aliphatic radical of 1 to 4 carbon atoms and $R^4$ together with one radical $R^3$ may also be $-CH_2-CH_2-CH_2-$, and/or dimethylsulfoxide, the percentages stated being based on methyl vinyl ketone.

The reaction can be represented by the following equations:

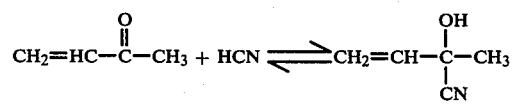

The process of the invention is based on the observation that the synthesis of vinyl-lactonitrile gives optimum results, compared to the prior art, not in the absence of solvents or in the presence of very small amounts of solvents, but when using the amounts of solvent according to the present invention, together with low amounts of hydrogen cyanide. Compared to the conventional processes, the process according to the invention gives vinyl-lactonitrile in a simple and economical manner, and in better yield and greater purity. The use of a large excess of hydrogen cyanide is avoided; the process is safer, causes less pollution of the environment, can be regulated more easily and is hence simpler to operate, particularly on an industrial scale. Greater safety of operation results from the fact that it is possible, without hazard, to allow the reaction mixture to react adiabatically in the event of a fault, for example in the event of failure of the cooling. Under such conditions, solvent-free batches spontaneously rise to at least 170° C., with accompanying rise of pressure. In stirred kettles operated at atmospheric pressure, this would result in extremely dangerous leakages of hydrogen cyanide (Example 28). Greater ease of regulating, on the other hand, results from the greater ease of removing the heat if the reaction is carried out in solvents, and from the fact that the very small amounts of catalyst used can be diluted beforehand. Further advantages result if the cyanohydrins formed are processed further in the same medium, for example by hydrolysis in water, by alcoholysis in alcohols or by polymerization in, for example, alcohols or carboxylic acid amides. A further advantage of the process according to the invention is that the addition reaction of excess hydrogen cyanide at the C=C double bond of vinyl-lactonitrile, to give α-methyl-α-hydroxyglutarodinitrile

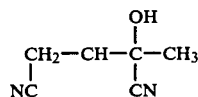

which is observed in solvent-free reaction mixtures, virtually does not occur, even with lengthy residence times, in the process according to the invention. These advantageous results are surprising in view of the above processes which employ very dilute cyanohydrin solutions, since extensive dissociation of the end product formed, increased formation of by-products and decomposition products, and hence a reduced yield, would also have been expected under the conditions according to the invention. Both vinyl-lactonitrile and hydrogen cyanide very readily undergo chemical changes in an alkaline medium, above all in the presence of water.

The liquid hydrogen cyanide is employed in an amount of from 1 to 1.2, preferably from 1 to 1.1, moles per mole of methyl vinyl ketone. The reaction is carried out in the presence of basic compounds, preferably in an amount of from 0.001 to 0.1, especially from 0.005 to 0.05, equivalent per mole of methyl vinyl ketone. Preferred basic compounds are alkali metal compounds, alkaline earth metal compounds and especially tertiary amines, as well as mixtures of these. Advantageous alkali metal compounds and alkaline earth metal compounds to use are the hydroxides, alcoholates, oxides, carbonates, bicarbonates, cyanides and salts with weak or polybasic acids, of calcium, barium, magnesium, lithium and, in particular, sodium and potassium. Examples of advantageous basic compounds are potassium hydroxide, sodium hydroxide, sodium methylate, potassium carbonate, potassium cyanide, sodium carbonate, lithium carbonate, sodium bicarbonate, potassium bicarbonate, calcium hydroxide, barium oxide, magnesium hydroxide, calcium carbonate, sodium acetate, trimethylamine, triethylamine, tripropylamine, tributylamine, pyridine, diethylaniline, dimethylaminoethanol, N-ethylpiperidine, N-methylpyrrolidine, dimethylaniline and quinoline. Basic ion exchangers can also be used.

The reaction can be carried out in the presence of one or more organic solvents, used by themselves or mixed with water, or in the presence of water alone.

The preferred solvents are water and compounds of the formulae II and III, where $R^1$ is alkyl of 1 to 12, preferably of 1 to 5, carbon atoms, chloroalkyl of 1 to 12, preferably of 1 to 5, carbon atoms, or hydroxyalkyl of 1 to 12, preferably of 1 to 5, carbon atoms, which may additionally contain 1 or 2 ether bridges —O— and which preferably has the hydroxyl group in the ω-position relative to $OR^2$, $R^2$ is alkyl, chloroalkyl or hydroxyalkyl of 1 to 6, preferably of 1 to 4, carbon atoms (the hydroxyl group in hydroxyalkyl being advantageously in the ω-position) or is hydrogen or

$R^1$ and $R^2$ together may also be —CH$_2$—CH$_2$—CH$_2$—CH$_2$— or —CH$_2$—CH$_2$—O-CH$_2$—CH$_2$—, the individual radicals $R^3$ and $R^4$ may be identical or different and each is hydrogen or alkyl of 1 to 4 carbon atoms, and $R^4$ together with one radical $R^3$ may also be —CH$_2$—CH$_2$—, and/or dimethylsulfoxide.

Advantageous solvents include water; ethylene chlorohydrin; methyl, ethyl, n-propyl, isopropyl, n-butyl, isobutyl, tert.-butyl and sec.-butyl formate; formamide and N-methyl-, N-ethyl-, N-n-propyl-, N-isopropyl-, N-n-butyl-, N-isobutyl-, N-tert.-butyl- and N-sec.-butyl-formamide; formamides which are disubstituted at the nitrogen by methyl, ethyl, n-propyl, isopropyl, n-butyl, isobutyl, tert.-butyl or sec.-butyl; monosubstituted pyrrolidones; dimethylsulfoxide; ethyl propyl ether, methyl tert.-butyl ether, n-butyl ethyl ether, di-n-propyl ether, dimethyl ether, di-n-butyl ether, diisobutyl ether, diisoamyl ether, diisopropyl ether, diethyl ether, tetrahydrofuran and dioxane; ethylene glycol, 1,2-propylene glycol, 1,3-propylene glycol, 1,2-butanediol, 1,4-butanediol, 2,3-butanediol, 1,3-butanediol, diethylene glycol, triethylene glycol and tetraethylene glycol, which are unsubstituted, or mono-etherified by methyl, ethyl, n-propyl, isopropyl, n-butyl, isobutyl, sec.-butyl or tert.-butyl or di-etherified by two identical or different groups from this list; corresponding polyglycols with 1,2-propylene glycol, with or without ethylene glycol, as chain members, and their correspondingly substituted monoethers and diethers; ethanol, methanol, n-butanol, isobutanol, tert.-butanol, n-propanol, isopropanol, pentanol, hexanol, octanol, heptanol and nonyl alcohol; fatty alcohols, e.g. decyl alcohol, undecyl alcohol and dodecyl alcohol; 2-ethylhexanol; isooctanol, isononanol, isodecanol and mixtures of these; and mixtures of liquid fatty alcohols, which are manufactured on a large scale by hydrogenating natural fats and oils or by reducing synthetic paraffincarboxylic acids and their esters or by oxidizing paraffins or by hydrolyzing esters such as sperm oil. The mixtures of higher alcohols obtained from the oxo reaction, with subsequent reduction of the fatty alcohol mixtures obtained, and corresponding mixtures obtained by synthesis using carbon monoxide and hydrogen, for example obtained from the Synthol process or the Alfol process, may also be used. For a definition of fatty alcohols and the manufacture of the starting compounds II, reference may be made to Ullmanns Encyklopädie der technischen Chemie, volume 7, pages 437 et seq., volume 13, pages 60 et seq., volume 3, pages 289 et seq. and supplementary volume, pages 86 et seq. The preferred solvents are especially those in the Examples.

The reaction is carried out in the presence of from 50 to 1,500, preferably from 50 to 1,000, and especially from 50 to 500, percent by weight of compound II, especially from 50 to 1,000 percent by weight, preferably from 50 to 500 percent by weight, of an alkanol II of 1 to 4 carbon atoms, from 150 to 1,000 percent by weight, preferably from 200 to 500 percent by weight, of an alkanol II of 5 to 8 carbon atoms, from 300 to 1,000 percent by weight, preferably from 250 to 500 percent by weight, of an alkanol II of 9 to 12 carbon atoms, from 50 to 500 percent by weight, preferably from 100 to 500 percent by weight, of an ω-chloroalkanol II of 1 to 4 carbon atoms, from 50 to 1,000 percent by weight, preferably from 80 to 500 percent by weight, of a diol or ether-diol II of 2 to 6 carbon atoms, from 100 to 1,000 percent by weight, preferably from 150 to 500 percent by weight, of a diol or ether-diol II of 7 to 12 carbon atoms, from 50 to 1,000 percent by weight, preferably from 100 to 500 percent by weight, of a formic acid ester II, an ether or cyclic ether II or an ether-monoalkanol II, from 10 to 1,000 percent by weight, preferably from 50 to 500 percent by weight, of a carboxylic acid amide III or dimethylsulfoxide, or from 3 to 100 percent by weight, preferably from 3 to 30 percent by weight, of water, the percentages being based on methyl vinyl ketone. In the case of mixtures with water, the above general and preferred percentages of organic solvent apply; in the case of mixtures of several organic solvents, the above general and preferred values for the solvent component with the widest range in respect of amount by weight to be used in the mixture apply.

The reaction is in general carried out at from 0° to −50° C., preferably from −5° C. to −45° C., under atmospheric or superatmospheric pressure, continuously or batchwise.

The reaction can be carried out as follows: a mixture of methyl vinyl ketone, hydrogen cyanide, solvent and basic compound is kept at the reaction temperature for from 0.5 to 4 hours. The vinyl-lactonitrile is then isolated from the mixture in the conventional manner, for example by acidifying the mixture, for example with phosphoric acid, and fractionally distilling it. The yield can be determined by introducing a sample of the reaction solution, with thorough stirring, into an excess of N/20 silver nitrate solution (acidified with $HNO_3$) and back-titrating the unconverted $AgNO_3$ potentiometrically with N/10 HCl solution. Advantageously, the unconverted hydrogen cyanide is immediately precipitated as AgCN. The values obtained can be confirmed by polarographic determination of the unconverted methyl vinyl ketone at pH 2.

In a preferred, particularly economical embodiment, the reaction is first carried out at from −10° C. to −20° C., after which the temperature is lowered further, to from −30° to −50° C. This procedure in most cases increases the yield. Surprisingly, even at these very low temperatures the equilibrium is set up sufficiently rapidly to give a system which is of economic interest. Accordingly, if the process is carried out continuously in a stirred kettle cascade with at least two stages, the temperature in the first stirred kettle is set to from −10° to −20° C. whilst in the next stirred kettle the reaction is completed at from −30° to −50° C., preferably at from −40° C. to −50° C.

The compounds obtainable by the process of the invention are valuable starting materials for the manufacture of drugs, crop protection agents, dyes, plastics and synthetic resins. Regarding their uses, reference may be made to the above publication and to U.S. Pat. No. 2,812,315.

In the Examples which follow, parts are by weight.

EXAMPLE 1

(a) 13.5 parts of liquid hydrogen cyanide and 40 parts of n-butanol are introduced into a stirred vessel and 35 parts of methyl vinyl ketone are added in the course of 2 minutes at −20° C. 0.5 part of triethylamine is then passed slowly into the mixture in the course of 15 minutes at −25° C., after which the colorless mixture is kept at −10° C. for 45 minutes. 39.6 parts (81.5% of theory) of α-vinyl-lactonitrile are obtained, as determined titrimetrically. After acidifying the reaction mixture with phosphoric acid, the end product is isolated by fractional distillation; it boils at 45°–46° C./0.25 mm Hg.

(b) Comparison: The reaction is carried out as in Example 1(a) but without n-butanol. 38.4 parts (79% of theory) of α-vinyl-lactonitrile are obtained. If the reaction is carried out with 40 parts of (b1) toluene, (b2) 1,2-dichloroethane or (b3) 1-nitropropane, instead of butanol, the yields are, respectively, (b1) 69% of theory, (b2) 69.5% of theory and (b3) 70.5% of theory.

EXAMPLES 2 TO 25

The reaction is carried out as in Example (1a) with the solvents shown in Table 1 in place of n-butanol. In Examples 4, 8, 19, 21, 22 and 25 the reaction is carried out at −40° C. instead of at −25° C., and in Example 13 at −10° C. The fatty alcohol mixture in Example 7 is a mixture of alkanols of 9 and 11 carbon atoms, in the weight ratio of 1:1, obtained from an oxo reaction.

TABLE 1

| Example No. | Parts | Solvent | Yield of vinyl-lactonitrile in % of theory |
|---|---|---|---|
| 2 | 64 | Methanol | 84.5 |
| 3 | 68 | n-Butanol | 83.0 |
| 4 | 80 | iso-Butanol | 90.7 |
| 5 | 40 | tert.-Butanol | 83.0 |
| 6 | 80 | Pentanol | 81.0 |
| 7 | 100 | Fatty alcohol mixture | 80.0 |
| 8 | 18 | Methanol | 93.0 |
| 9 | 80 | Ethylene glycol | 84.5 |
| 10 | 40 | Pentanediol | 85.5 |
| 11 | 80 | Ethylene chlorohydrin | 80.5 |
| 12 | 80 | Isobutyl formate | 82.0 |
| 13 | 9 | Water | 82.0 |
| 14 | 20 | Formamide | 83.0 |
| 15 | 40 | Dimethylformamide | 88.0 |
| 16 | 40 | N-Methylpyrrolidone | 92.0 |
| 17 | 40 | Tetrahydrofuran | 83.0 |
| 18 | 40 | Dioxane | 84.0 |
| 19 | 55 | Isopropanol | 92.5 |
| 20 | 40 | Methylglycol | 82.0 |
| 21 | 55 | n-Propanol | 93.0 |
| 22 | 50 | Ethanol | 93.0 |
| 23 | 40 | Dimethylsulfoxide | 92.5 |
| 24 | 40 / 40 | n-Butanol + / n-butyl formate | 80.5 |
| 25 | 65 / 5 | n-Butanol + / $H_2O$ | 92.0 |

EXAMPLE 26

The procedure followed is as in Example 2, but instead of triethylamine 1.7 parts of a 50 percent strength by weight aqueous potassium carbonate solution are used as the catalyst. 40.7 parts of vinyl-lactonitrile (84% of theory) are obtained.

EXAMPLE 27

The procedure followed is as in Example 1, but 40 parts of n-propanol are used instead of n-butanol, and 1.0 part of a 40 percent strength by weight aqueous potassium cyanide solution is used as the catalyst. 40 parts of vinyl-lactonitrile (82.5% of theory) are obtained.

COMPARATIVE EXAMPLE 28

(a) 400 parts of the reaction mixture prepared as in Example 3 are left to stand at $-10°$ C. The temperature of the mixture reaches $+20°$ C. after 2½ hours, $+60°$ C. after a further hour and $100°$ C. 30 minutes thereafter. After cooling, the pale yellow mixture is worked up by distillation. Levulonitrile is obtained in a yield of 90% of theory.

(b) Comparison: 10 percent by weight of a mixture of 245 parts of methyl vinyl ketone and 108 parts of hydrogen cyanide are taken and the reaction is started by slowly adding 0.35 part of triethylamine thereto. The remaining 90 percent by weight of the mixture are then added slowly, in the course of 45 minutes, synchronously with 3.15 parts of triethylamine, whilst maintaining the internal temperature at $-10°$ C. by means of external cooling. The mixture is allowed to react for a further hour and is then transferred into a metal pressure vessel which is heat-insulated and has been precooled to $-10°$ C. The pressure vessel is sealed and the temperature rise and pressure rise are followed; $0°$ C. is reached after 2 hours, and the temperature then rises in the course of 10 minutes to $170°$ C. whilst the pressure rises to 3 atmospheres gauge.

I claim:

1. A process for the manufacture of vinyl-lactonitrile of the formula

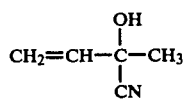

comprising:
reacting methyl vinyl ketone with from 1 to 1.2 moles of hydrogen cyanide per mole of methyl vinyl ketone in the presence of an effective amount of at least one basic compound as a catalyst selected from the group consisting of alkali metal compound, alkaline earth metal compound, and tertiary amine at a temperature from $0°$ to $-50°$ C., in the presence of:

from 300 to 1000 percent by weight, based on methyl vinyl ketone, of a compound which is an alkanol of 9 to 12 carbon atoms, or in the presence of:

from 50 to 500 percent by weight, based on methyl vinyl ketone, of ω-chloroalkanol of 1 to 4 carbon atoms, or in the presence of:

from 50 to 1000 percent by weight, based on methyl vinyl ketone, of diol or ether diol of 2 to 6 carbon atoms, or in the presence of:

from 100 to 1000 percent by weight, based on methyl vinyl ketone, of diol or ether diol of 7 to 12 carbon atoms, or in the presence of:

from 50 to 500 percent by weight, based on methyl vinyl ketone, of carboxylic acid amides of the formula

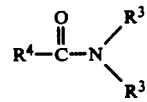

where the individual radicals $R^3$ and $R^4$ are identical or different and each is hydrogen or an alkyl of 1 to 4 carbon atoms and $R^4$ together with one radical $R^3$ may also be $-CH_2-CH_2-CH_2-$, or in the presence of:

from 50 to 500 percent by weight, based on methyl vinyl ketone, of dimethylsulfoxide, or in the presence of:

from 3 to 30 percent by weight of water, based on methyl vinyl ketone, or mixtures of the above.

2. A process as set forth in claim 1, wherein the reaction is carried out in the presence of from 50 to 500 percent by weight, based on methyl vinyl ketone, of ω-chloroalkanol of 1 to 4 carbon atoms.

3. A process as set forth in claim 1, wherein the reaction is carried out in the presence of from 50 to 1000 percent by weight, based on methyl vinyl ketone, of diol or ether diol of 2 to 6 carbon atoms.

4. A process as set forth in claim 1, wherein the reaction is carried out in the presence of from 100 to 1000 percent by weight, based on methyl vinyl ketone, of diol or ether diol of 7 to 12 carbon atoms.

5. A process as set forth in claim 1, wherein the reaction is carried out in the presence of from 50 to 500 percent by weight, based on methyl vinyl ketone, of carboxylic acid amides according to formula III or dimethylsulfoxide.

6. A process as set forth in claim 1, wherein the reaction is carried out in the presence of from 3 to 30 percent by weight, based on methyl vinyl ketone, of water.

7. A process as set forth in claim 1, wherein the reaction is carried out in the presence of from 300 to 1000 percent by weight, based on methyl vinyl ketone, of an alkanol of 9 to 12 carbon atoms.

8. A process as set forth in claim 1, wherein the reaction is carried out at from $-5°$ to $-45°$ C.

9. A process as set forth in claim 1, wherein the reaction is carried out first at $-10°$ C. to $-20°$ C., and then at from $-30°$ C. to $-50°$ C.

10. A process as set forth in claim 1, wherein the reaction is carried out in a mixture of solvents.

* * * * *